United States Patent
Kang et al.

(10) Patent No.: US 9,895,060 B2
(45) Date of Patent: Feb. 20, 2018

(54) APPARATUS AND METHOD FOR ANALYZING BIOSIGNAL

(71) Applicant: SAMSUNG ELECTRONICS CO., LTD., Suwon-si (KR)

(72) Inventors: Jaemin Kang, Seoul (KR); Yongjoo Kwon, Yongin-si (KR); Sunkwon Kim, Suwon-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 0 days.

(21) Appl. No.: 14/980,736

(22) Filed: Dec. 28, 2015

(65) Prior Publication Data

US 2017/0007125 A1    Jan. 12, 2017

(30) Foreign Application Priority Data

Jul. 8, 2015 (KR) .......................... 10-2015-0097416

(51) Int. Cl.
*A61B 5/00* (2006.01)
*A61B 5/021* (2006.01)
(Continued)

(52) U.S. Cl.
CPC .......... *A61B 5/0002* (2013.01); *A61B 5/0024* (2013.01); *A61B 5/0261* (2013.01); *A61B 5/02108* (2013.01); *A61B 5/681* (2013.01); *A61B 5/6898* (2013.01); *A61B 5/7278* (2013.01); *A61B 5/7285* (2013.01); *A61B 5/746* (2013.01); *A61B 5/02007* (2013.01); *A61B 5/02035* (2013.01); *A61B 5/6802* (2013.01)

(58) Field of Classification Search
CPC .......................... A61B 5/0002; A61B 5/0024
USPC ....................................................... 340/870.07
See application file for complete search history.

(56) References Cited

U.S. PATENT DOCUMENTS

2002/0198443 A1* 12/2002 Ting ................... A61B 5/14552
600/323
2010/0191074 A1* 7/2010 Chou .................. A61B 5/0002
600/301
(Continued)

FOREIGN PATENT DOCUMENTS

JP        4805726 B2    11/2011
KR   10-1038432 B1     6/2011
(Continued)

OTHER PUBLICATIONS

Communication dated Nov. 14, 2016 issued by the European Patent Office in counterpart European Patent Application No. 16178115.8.

*Primary Examiner* — Qutbuddin Ghulamali
(74) *Attorney, Agent, or Firm* — Sughrue Mion, PLLC

(57) ABSTRACT

An apparatus for analyzing a biosignal is provided. The apparatus includes a communicator configured to receive from an external device a first biosignal of an object detected by the external device; a synchronizer configured to transmit a synchronization signal to from the external device or receive the synchronization signal from the external device; at least one biosignal detector configured to detect a second biosignal of the object according to the synchronization signal; and a processor configured to compare characteristics of the first biosignal and the second biosignal and obtain biometric information having correlation with a result of the comparison.

21 Claims, 19 Drawing Sheets

(51) Int. Cl.
     *A61B 5/026*     (2006.01)
     *A61B 5/02*      (2006.01)

(56) References Cited

U.S. PATENT DOCUMENTS

| | | | |
|---|---|---|---|
| 2014/0275824 A1* | 9/2014 | Couse | A01K 29/005 600/301 |
| 2014/0275888 A1* | 9/2014 | Wegerich | A61B 5/6831 600/324 |
| 2014/0276145 A1 | 9/2014 | Banet et al. | |
| 2016/0220194 A1 | 8/2016 | Kang et al. | |

FOREIGN PATENT DOCUMENTS

| | | |
|---|---|---|
| KR | 10-1260465 B1 | 5/2013 |
| KR | 10-1273619 B1 | 6/2013 |
| KR | 10-2016-0094218 A | 8/2016 |
| WO | 20012/140559 A1 | 10/2012 |

\* cited by examiner

APPARATUS AND METHOD FOR ANALYZING BIOSIGNAL

CROSS-REFERENCE TO RELATED APPLICATION

This application claims priority from Korean Patent Application No. 10-2015-0097416, filed on Jul. 8, 2015 in the Korean Intellectual Property Office, the disclosure of which is incorporated herein by reference in its entirety.

BACKGROUND

1. Field

Apparatuses and methods consistent with exemplary embodiments relate to obtaining biometric information from biosignals detected by mutually independent apparatuses.

2. Description of the Related Art

Due to medical development, people's average life span is increasing. Their increased interest and management in health as well as the medical development have contributed to the increase of the average life span.

As various medical devices for checking health have been developed, people may directly check their own health without going to a doctor's office or a hospital. Accordingly, various kinds of biosignal analyzing apparatuses are being developed. Combinations of an apparatus for healthcare with a device carried by a subject are being developed.

Generally, methods for detecting biometric information, such as pulse waves, may include invasive methods and non-invasive methods. Recently, non-invasive methods of easily detecting pulse waves without inflicting pain to a subject are widely used.

For accurate pulse wave analysis (PWA), information may be obtained from optical signals or pressure signals at a fixed location on the body surface. Biometric information regarding a subject may be obtained based on such information, where various methods are used to reduce measurement errors.

SUMMARY

One or more exemplary embodiments provide an apparatus for analyzing biosignals detected by the apparatus and another apparatus which are separate from each other and independently operated.

Further, one or more exemplary embodiments provide methods of analyzing biosignals detected by apparatuses separate and independent from each other.

According to an aspect of an exemplary embodiment, there is provided an apparatus for analyzing a biosignal including: a communicator configured to receive from an external device a first biosignal of an object detected by the external device; a synchronizer configured to transmit a synchronization signal to the external device or receive the synchronization signal from the external device; at least one biosignal detector configured to detect a second biosignal of the object according to the synchronization signal; and a processor configured to compare characteristics of the first biosignal and the second biosignal and obtain biometric information having correlation with a result of the comparison.

The apparatus may be a type of apparatus different from the external device.

The apparatus may be portable or wearable by the object, and independent from the external device.

The apparatus may correspond to a smartphone or a smartwatch.

The first biosignal and the second biosignal may include pulse wave signals.

The processor may be further configured to obtain a pulse wave velocity based on the characteristics of the first biosignal and the second biosignal.

The biometric information may include at least one of blood pressure, blood vessel elasticity, blood viscosity, artery stiffness, and blood flow rate.

The at least one biosignal detector may include a plurality of biosignal detectors, and the apparatus may further include a biosignal selection unit configured to select one of the plurality of biosignal detectors and control the selected biosignal detector to detect the second biosignal of the object while the selected biosignal detector is in contact with the object.

The apparatus may further include a memory configured to store the obtained biometric information, and the processor may be further configured to determine an average biometric information range based on the stored biometric information and store the average biometric information range in the memory.

The apparatus may further include an alarm unit configured to generate an alarm when newly obtained biometric information is outside the average biometric information range.

The processor may be configured to obtain a pulse wave transit time between two points corresponding to a peak point of the first biosignal and a peak point of the second biosignal.

According to an aspect of another exemplary embodiment, there is provided an apparatus for analyzing a biosignal, the apparatus including: at least one biosignal detector configured to detect a biosignal of an object; a communicator configured to transmit the biosignal or data obtained by processing the biosignal to an external device; and a synchronizer configured to synchronize the at least one biosignal detector with a biosignal detector of the external device.

The apparatus may be independently operated from the external device.

The biosignal may include a pulse wave signal.

According to an aspect of another exemplary embodiment, there is provided an apparatus for analyzing a biosignal, the apparatus including: a first apparatus including at least one first biosignal detector configured to detect a first biosignal of an object, a first synchronization signal generator, and a first processor configured to obtain biometric information by processing a biosignal; and a second apparatus including a first synchronization signal receiver configured to receive a synchronization signal from the first synchronization signal generator, at least one second biosignal detector configured to detect a second biosignal of the object according to the synchronization signal, and a first communicator configured to transmit the second biosignal to the first processor, wherein the first apparatus is configured to compare characteristics of the first biosignal and the second biosignal and obtain the biometric information based on a result of the comparison.

The first apparatus may further include a second receiver and a second communicator, the second apparatus may further include a second synchronization signal generator and a second processor, and at least one of the first apparatus and the second apparatus may further include a master setting unit configured to select a master processor performing signal processing from among the first processor and the second processor.

The first apparatus and the second apparatus may be different types of mobile apparatuses.

At least one of the first apparatus and the second apparatus is a wearable mobile apparatus.

One of the first apparatus and the second apparatus may be wearable by the object, and the other one of the first apparatus and the second apparatus may be a portable apparatus which is in contact with the object while the first biosignal or the second biosignal is detected.

The first apparatus may be a mobile apparatus portable by the object, and the second apparatus may be a mobile apparatus wearable by the object.

The first apparatus may further include a first biosignal selection unit, wherein the at least one first biosignal detector may include a plurality of first biosignal detectors that contact the object, and the first biosignal selection unit may select one of the plurality of first biosignal detectors and control the selected first biosignal detector to detect the first biosignal.

The at least one second biosignal detector may include a plurality of second biosignal detectors, and the second apparatus may further include a second biosignal selection unit configured to select one of the plurality of second biosignal detectors and control the selected second biosignal detector to detect the second biosignal.

According to an aspect of another exemplary embodiment, there is provided a method of analyzing a biosignal by a first apparatus, the method including: detecting a first biosignal by a first biosignal detector of the first apparatus; receiving a second biosignal from a second apparatus; comparing characteristics of the detected first biosignal and the received second biosignal by a processor of the first apparatus; and obtaining biometric information based on a result of the comparison by the processor.

According to an aspect of another exemplary embodiment, there is provided a method of analyzing a biosignal of an object by a first apparatus and a second apparatus which is provided separately from the first apparatus, the method including: generating a synchronization signal by a first synchronizer of the first apparatus; detecting a first biosignal according to the synchronization signal by a first biosignal detector of the first apparatus while the first apparatus is in contact with the object; detecting a second biosignal according to the synchronization signal by a second biosignal detector of the second apparatus while the second apparatus is within a predetermined distance range from the first apparatus; transmitting the second biosignal from the second apparatus to the first apparatus; extracting, by a first processor of the first apparatus, a first feature point of the first biosignal and a second feature point of the second biosignal that corresponds to the second feature point; and obtaining biometric information based on the first feature point and the second feature point.

BRIEF DESCRIPTION OF THE DRAWINGS

The above and/or other aspects will be more apparent by describing certain exemplary embodiments, with reference to the accompanying drawings, in which.

DETAILED DESCRIPTION

Figure 1:
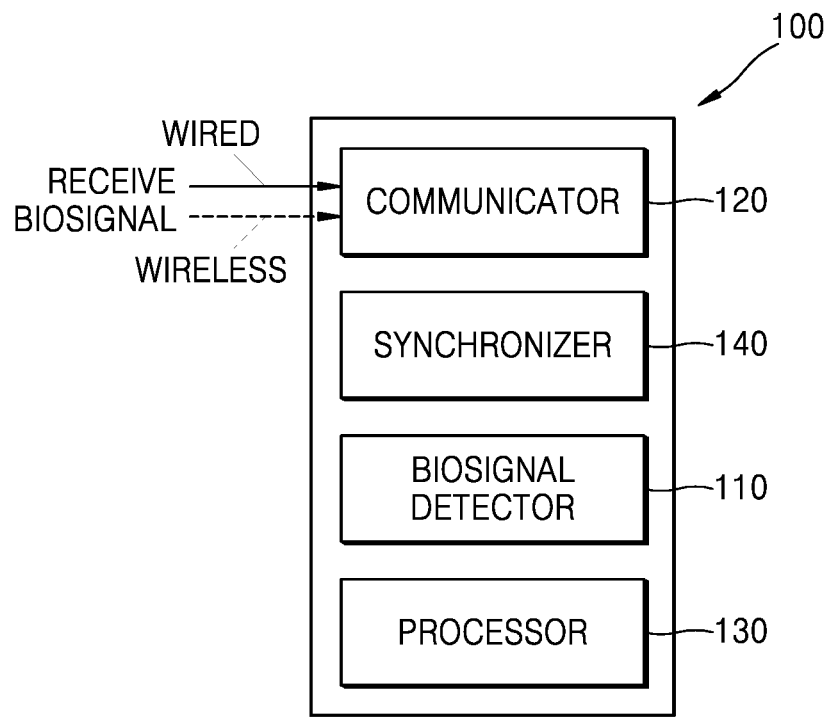
FIG. 1 schematically illustrates an apparatus for analyzing a biosignal, according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

It will be understood that, although the terms first, second, etc. may be used herein to describe various elements, these elements should not be limited by these terms. These terms are only used to distinguish one element from another.

As used herein, the singular forms "a", "an" and "the" are intended to include the plural forms as well, unless the context clearly indicates otherwise. It will be further understood that when a part "includes" or "comprises" an element, unless otherwise defined, the part may further include other elements, not excluding the other elements.

Also, the terms, such as "-er", "-or", "unit", or "module", should be understood as a unit for processing at least one function or operation and that may be embodied in a hardware manner, a software manner, or a combination of the hardware manner and the software manner. In addition, the description "A being provided in B" may be construed as meaning that A is provided in B so as to be in contact with B or to be in no contact with B.

FIG. 1 schematically illustrates an apparatus 100 for analyzing a biosignal, according to an exemplary embodiment.

The apparatus 100 may include a biosignal detector 110 detecting a first biosignal from an object, a communicator 120 receiving a second biosignal transmitted from another device, and a processor 130 processing the first biosignal and the second biosignal to obtain biometric information.

The biosignal may include an electrical signal or a waveform signal that may be measured as the biosignal detector 110 comes into contact with a human body. The biosignal may be also measured when the biosignal detector 110 is in the proximity of the human body. For example, the biosignal may include a pulse wave signal.

The apparatus 100 may detect biosignals at two points of a subject and may obtain information that may be derived from the biosignals and biometric information correlated to the information. When the biosignals at the two points are detected, a biosignal measured by the apparatus 100 and another biosignal transmitted from another device may be used to obtain the biometric information.

The apparatus 100 may come into contact with the object to detect the first biosignal. The apparatus 100 may be embodied as one or more devices. For example, the apparatus 100 may be applied to a device used by the subject. Examples of the apparatus 100 may include a portable mobile device carried by the subject and a wearable mobile device worn by the subject. Examples of the portable mobile device may include a smartphone, and examples of the wearable mobile device may include a smartwatch and a wearable device made for medical purposes. However, the apparatus 100 is not limited thereto, and may be applied as one or more forms to an item often used by the subject.

The biosignal detector 110, for example, may detect a pulse wave signal of the object. The pulse wave signal may be detected by using a direct measurement method or an indirect measurement method. The direct measurement method, for example, may include a method in which pressure is used. The indirect measurement method may include a pulse transit time (PTT) method in which an optical signal and an electrocardiogram (ECG) signal are used, or a pulse wave analysis (PWA) method based on an optical signal. For example, the pulse wave signal of the object may be detected by using a measurement method in which light is used. The biosignal detector 110, which is a cuffless-type pulse wave signal detector, may radiate light on the object and may sense reflected or scattered light to measure a pulse wave.

Figure 2:
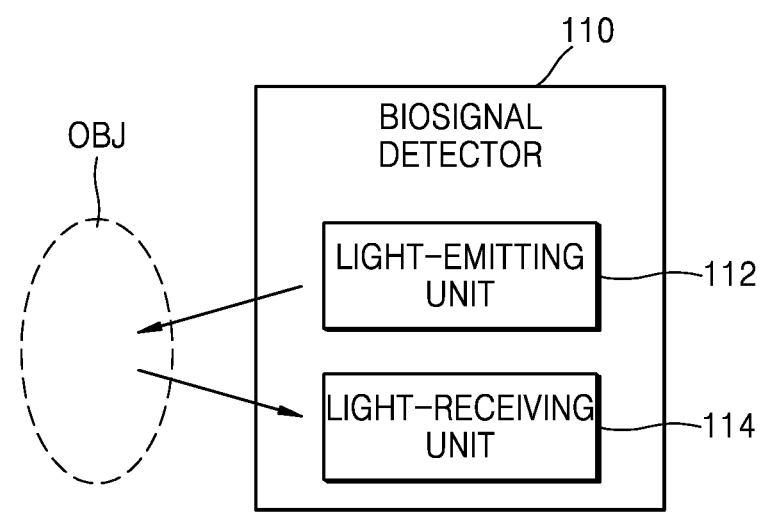
FIG. 2 illustrates an example of a biosignal detector of the apparatus of FIG. 1.

Referring to FIG. 2, the biosignal detector 110, for example, may include a light-emitting unit (e.g., light emitter) 112 and a light-receiving unit (e.g., light receiver) 114. The light-emitting unit 112 may radiate light on an object OBJ, and the light-receiving unit 114 may detect light scattered or reflected from the object OBJ. A pulse wave may be obtained from a detected optical signal.

Detecting a pulse wave signal will now be described as an example. Whenever blood spouts from the heart, changes in blood flow beat, pressure beat, and diameter beat may occur in arteries. A pulse of the arteries has a changed form as the pulse moves along the arteries whenever the heart contracts, and the form of the pulse may be determined by a cardiac output of the left ventricle, physical properties of the arterial wall, and properties of blood pressure. In a direction from the central artery to the peripheral artery, the average blood pressure has no significant change, whereas systolic blood pressure increases and diastolic blood pressure decreases, thereby increasing an amplitude of the pulse and changing a waveform of the pulse. Accordingly, such a wave pulse signal may be detected and analyzed, thereby obtaining various pieces of biometric information related to blood vessels.

The object OBJ for detecting biometric information, may be a biological part that may contact or be adjacent to the biosignal detector 110 and may be a part of a human body at which a pulse wave is easily measured by using photoplethysmography (PPG). For example, the object OBJ may be an area of a wrist surface that is adjacent to a radial artery portion. When a pulse wave is measured at a skin surface of a wrist underneath which the radial artery passes, the measurement of the pulse wave may be relatively less influenced by external factors which cause measurement errors, such as thickness of skin tissue in the wrist. Also, the radial artery is known as a blood vessel for measuring blood pressure at a relatively high accuracy compared to other blood vessels in the wrist. However, the object OBJ is not limited thereto, and may be other peripheral parts of the human body with a high blood vessel density, such as a finger, a toe, or an earlobe.

Figure 3A:
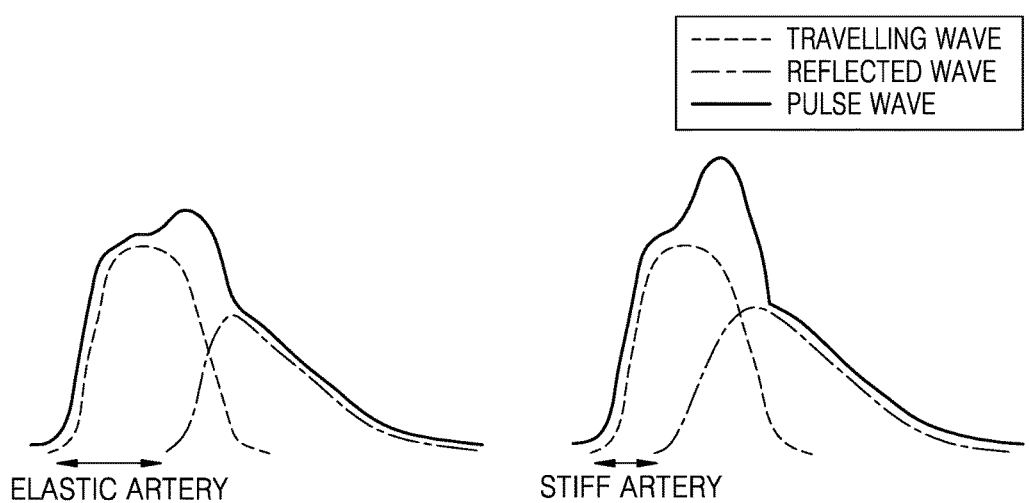
FIGS. 3A through 3C are diagrams showing examples of formation, shapes, and significance of pulse waves detected by a biosignal detector of an apparatus for analyzing a biosignal, according to an exemplary embodiment.
Figure 3B:
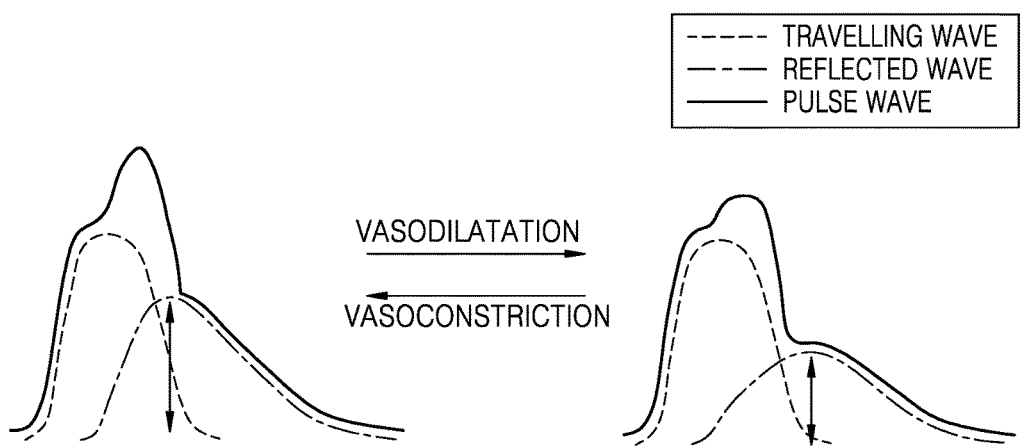
Figure 3C:
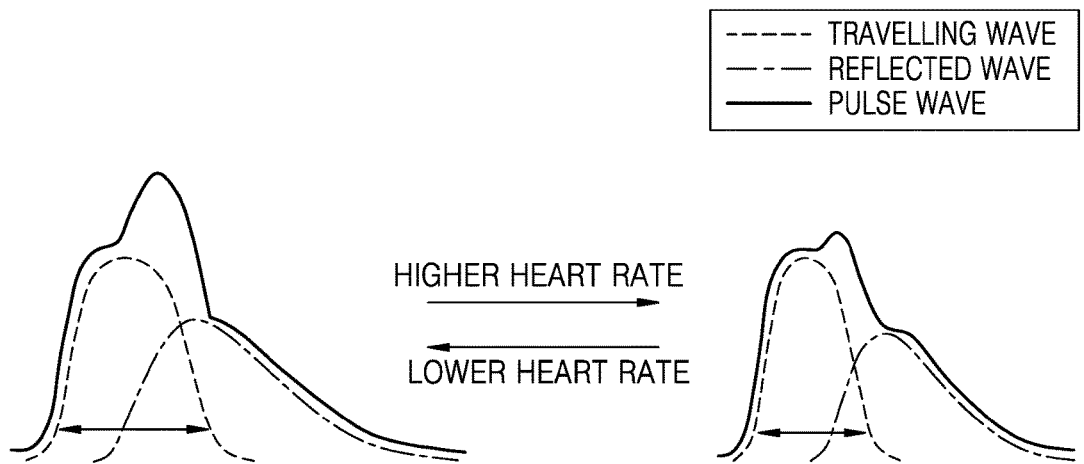
Figure 4:
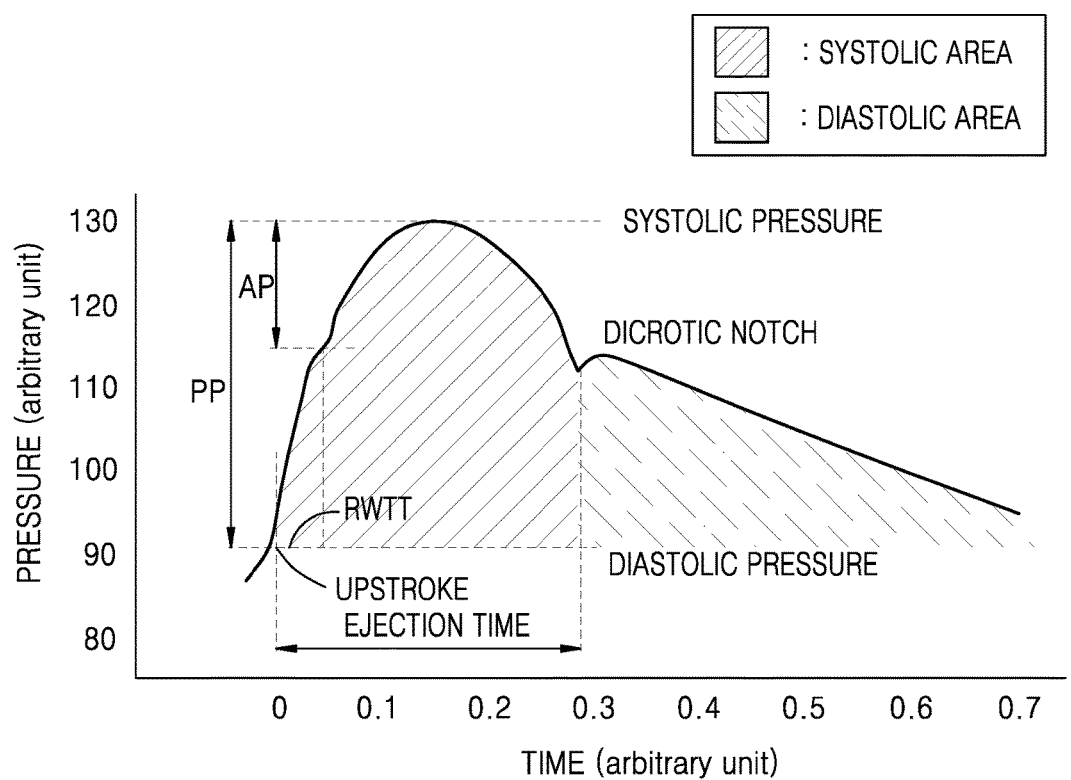
FIG. 4 is a diagram showing an example of biometric information that may be extracted from a waveform of a pulse wave.
Figure 5:
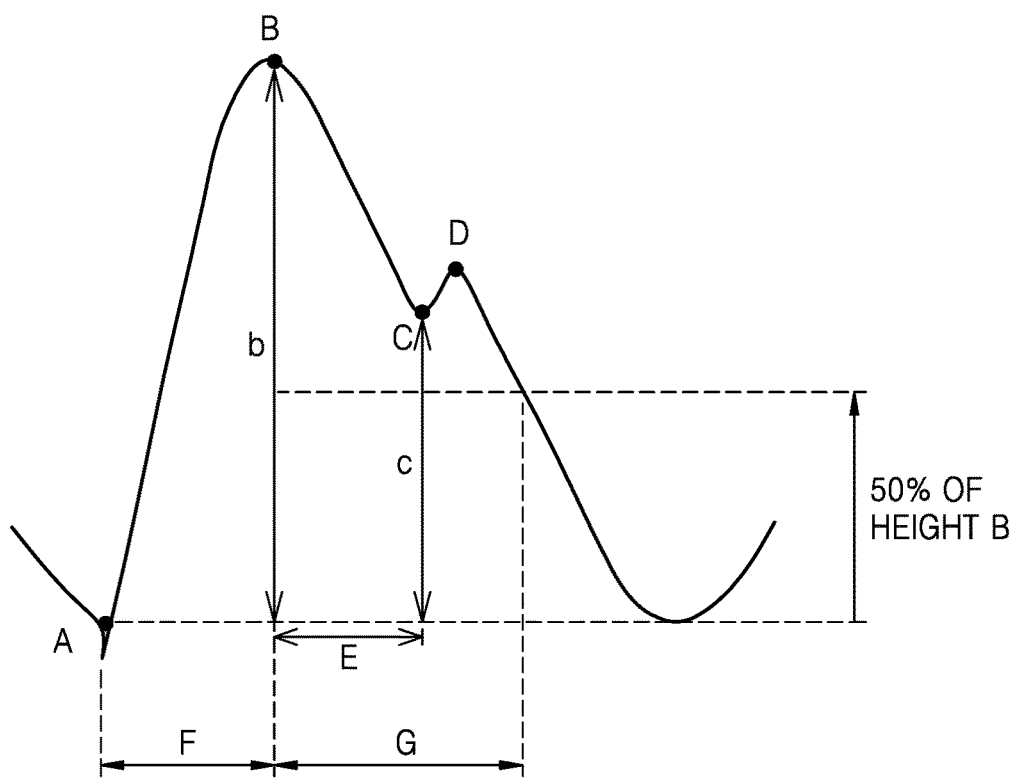
FIG. 5 is a diagram showing an example of pulse wave feature points extracted from a pulse wave signal.

FIGS. 3A through 3C are diagrams showing examples of formation and shapes of pulse waves of an apparatus for analyzing a biosignal, according to an exemplary embodiment. FIG. 4 is a diagram showing an example of biometric information that may be extracted from a waveform of a pulse wave. FIG. 5 is a diagram showing an example of pulse wave feature points extracted by the processor 130.

As shown in FIGS. 3A through 3C, traveling waves, which are generated by the heart and travel, and reflected waves, which are reflected by end portions and travel back, may overlap each other and thus constitute pulse waves. Pulse waves are augmented as reflected waves overlap traveling waves. Since forms of pulse waves reflect cardiovascular system conditions, blood pressures, or the like, various pieces of information may be obtained by using the PWA.

For example, FIG. 3A shows that the stiffer a blood vessel is, the faster a reflected wave arrives, where blood vessel stiffness may be determined based on a transit time of the reflected wave as an elastic artery, a stiff artery, etc. Furthermore, FIG. 3B shows that an amplitude of the reflected wave is related to expansion or contraction of the blood vessel, and FIG. 3C shows factors related to heartbeat rates. As shown in FIG. 3B, the amplitude of the reflected wave while blood vessels are contracted may be greater than the amplitude of the reflected wave while the blood vessels are widen. As shown in FIG. 3C, the time period which is taken for the travelling wave to complete one cycle may increase as the heart rate increases.

Referring to FIG. 4, an example of biometric information that may be extracted from a waveform of a pulse wave based on overlapping and augmentation of a traveling wave and a reflected wave is illustrated. For example, a pulse pressure (PP) is expressed as a difference between a systolic pressure and a diastolic pressure. A mean blood pressure is expressed as a diastolic pressure+PP/3 and may reflect a load on the heart. Furthermore, an augmentation pressure (AP) out of the PP (AP/PP) may be represented as a percentage (%) and may indicate an augmentation index (AI) that reflects elasticity of a blood vessel and a load of the left ventricle. A reflective wave transit time (RWTT) may reflect stiffness of a blood vessel. A subendocardial viability index (SERV) expressed as a diastolic area/systolic area may reflect coronary artery conditions, such as blood flow in the coronary artery or risk of any coronary artery disease. Furthermore, myocardial contractile force may be measured from an ejection time which is the time interval from the onset of the systolic upstroke to the dicrotic notch. Such indexes are related to diagnosis of a hypertension (determination of borderline hypertension), diagnosis of cardiac insufficiency (determination of systolic/diastolic dysfunctions), early diagnosis of cardiovascular system complications regarding diabetes, diagnosis of ischemic heart diseases, etc. and may be clinically utilized for improving efficiency of medicine prescriptions or treatments, where such indexes may be obtained by using invasive methods in the related art.

By taking into account such indexes, feature points A, B, C, and D may be extracted from an incidental wave and a reflective wave generated from a subject (e.g., human), as shown in FIG. 5. Transit time F, G, and I may be determined from feature points A, B, and D. Feature points may include, for example, a peak point or an inflection point in a pulse wave signal graph. FIG. 5 shows A, B, C, and D at locations related to the above descriptions as an example of the feature points, where more feature points may be added. Such feature points may be analyzed, and thus, biometric information may be derived therefrom. For example, feature points A, B, C, and D may correspond to the onset of the systolic upstroke, a peak systolic pressure, a dicrotic notch, and a peak dicrotic pressure, respectively. With reference with FIG. 5, the first peak B may be the incident pulse wave generated from the heart of the subject and the second peak D may be generated from the reflection of the incidental wave from a reflection site of the body. The peak-to-peak time (PPT) represents the transit time E between feature point B of the incidental wave and feature point D of the reflective wave. Since the travel distance of the reflective wave may be proportional to the height of the subject, a stiffness index (SI) may be calculated by dividing the height of the subject by the PPT (i.e., SI=height/PPT). The ratio of the amplitude of the reflective wave d to the amplitude of the incidental wave b may represent the reflective index (RI) (i.e., RI=d/b).

Figure 6:
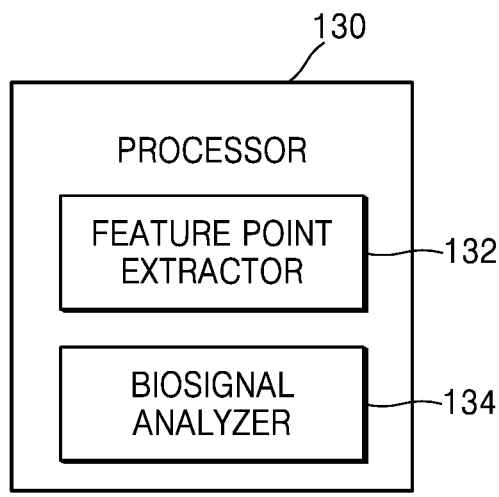
FIG. 6 illustrates an example of a processor of the apparatus of FIG. 1.

Referring to FIG. 6, the processor 130 may include a feature point extractor 132 extracting feature points from a detected biosignal and a biosignal analyzer 134 computing biometric information related to the feature points. For example, when a pulse wave signal is detected as a biosignal, the feature point extractor 132 of the processor 130 may extract predetermined feature points from a detected pulse wave. The feature points may be, for example, a peak point, an inflection point, or the like in a pulse wave signal graph. For example, the feature point extractor 132 may extract the feature points shown as an example in FIG. 5. The biosignal analyzer 134 may analyze feature points of the pulse wave signal and thus may obtain biometric information correlated to the feature points. For example, the biosignal analyzer 134 may find out PTT and pulse wave velocity from the feature points. Also, the biometric information may include, for example, at least one of blood pressure, blood vessel elasticity, blood viscosity, artery hardness, and blood flow rate.

The communicator 120 may communicate with another device. For example, the communicator 120 may receive a measured biosignal from the other device. In this regard, the other device may be an apparatus that is independently operated and separately provided from an apparatus including the biosignal detector 110. For example, the apparatus 100 may be applied to a portable terminal carried by the subject, and the other device may be a wearable terminal worn by the subject. Alternatively, the apparatus 100 may be applied to a wearable terminal worn by the subject, and the other device may be a portable terminal carried by the subject. The communicator 120 may receive a biosignal from the outside and also may transmit a biosignal to the other device. The communicator 120 may transmit and receive biosignals via wired or wireless communication.

The apparatus 100 may include a synchronizer 140 so that the biosignal detector 110 may detect a biosignal synchronizing with the other device detecting another biosignal. The synchronizer 140 may synchronize the biosignal and the other biosignal with respect to a time point when the biosignal detector 110 detects the biosignal and a time point when the other device detects the other biosignal so that a correlation expression may be extracted therefrom by combining or comparing the biosignals.

Figure 7:
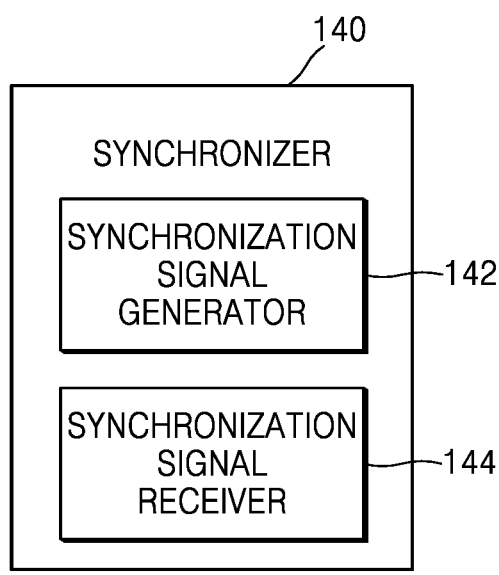
FIG. 7 illustrates an example of a synchronizer of the apparatus of FIG. 1.

Referring to FIG. 7, the synchronizer 140 may include, for example, a synchronization signal generator 142. Synchronization signals may be delivered to the biosignal detector 110 and a biosignal detector of another device. The synchronization signals may be transmitted via wired or wireless communication. In addition, the synchronizer 140 may include a synchronization signal receiver 144. A synchronization signal may be received from the other device and a biosignal may be detected.

Figure 8:
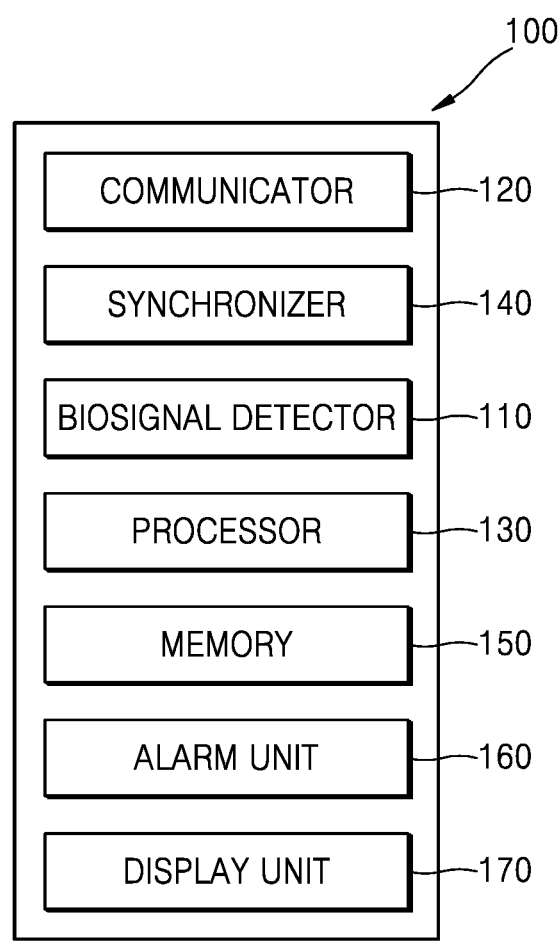
FIG. 8 schematically illustrates an apparatus for analyzing a biosignal, according to another exemplary embodiment.

FIG. 8 illustrates an example in which the apparatus 100 of FIG. 1 further includes a memory 150. The memory 150 may store pieces of biometric information obtained from the processor 130. The memory 150 may calculate an average biometric information range of an object from the stored pieces of biometric information and store the average biometric information range of the object. For example, when ten or more, or twenty or more pieces of biometric information regarding the object are stored, an average value thereof may be calculated, and a predetermined average biometric information range may be calculated with respect to the average value and stored. The average biometric information range may be, for example, a range of ±5% of the average value. However, this is just an example, and the average biometric information range may be determined from a medical perspective. The average biometric information range may continue to be updated based on recent data. Alternatively, the memory 150 may store a normal range of biometric information. For example, when the biometric information includes blood pressure, the memory 150 may include a normal blood pressure range.

The memory 150 may include at least one type of storage medium among a flash memory type, a hard disk type, a multimedia card micro type, a card type memory (for example, secure digital (SD) or extreme digital (xD) memory), random access memory (RAM), static random access memory (SRAM), read-only memory (ROM), electrically erasable programmable read-only memory (EEPROM), programmable read-only memory (PROM), a magnetic memory, a magnetic disk, and an optical disk.

Referring to FIG. 8, the apparatus 100 may further include an alarm unit 160. The alarm unit 160 may provide a notification to a subject (e.g., a user of the apparatus 100) when obtained biometric information is outside the average biometric information range. Alternatively, the alarm unit 160 may provide a notification to a subject (e.g., a user of the apparatus 100) when obtained biometric information is outside the normal biometric information range.

The alarm unit 160 may warn the subject of an abnormal biometric information analysis result by using a sound alarm, a text alarm, or the like.

Figure 9:
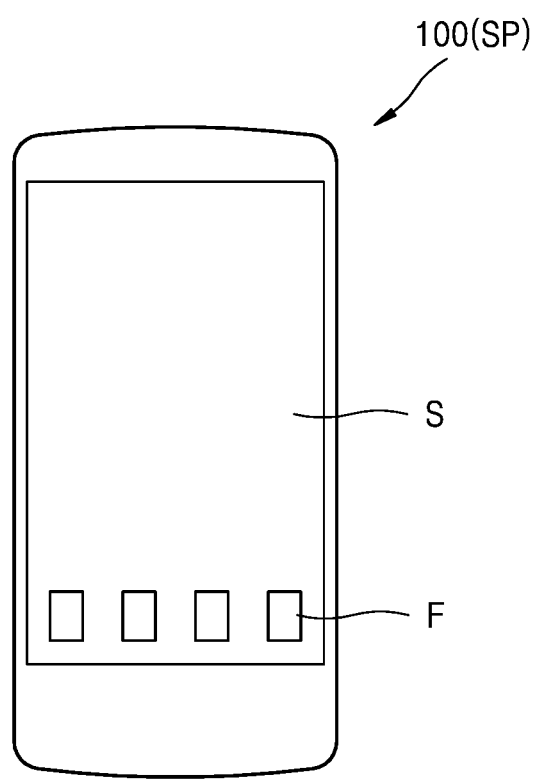
FIG. 9 illustrates an example in which an apparatus for analyzing a biosignal is applied to a smartphone.

The apparatus 100 may further include a display unit (e.g., display) 170 displaying obtained biometric information. The display unit 170 may display the biometric information and may also display alarm text, by the alarm unit 160, regarding abnormal biometric information. Referring to FIG. 9, when the apparatus 100 is applied, for example, to a smartphone SP, biometric information may be displayed on a screen S of the smartphone SP. Alternatively, obtained pieces of biometric information may be stored as files in a folder F of the smartphone SP. For example, date and time when a biosignal is detected, biometric information, and the like may be stored in the folder F. In addition, when the biometric information is outside a normal biometric information range or an average biometric information range of a subject, the alarm unit 160 may transmit the alarming contents to the smartphone SP by using text. Although a smartphone has been described herein as an example, the above description may be applied the same to another mobile device such as a smartwatch, as well.

Figure 10:
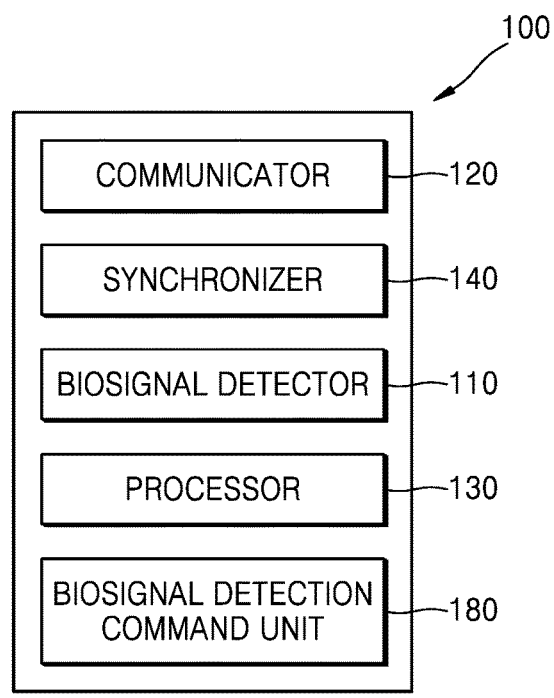
FIG. 10 illustrates an example in which the apparatus of FIG. 1 further includes a biosignal detection command unit.

Referring to FIG. 10, the apparatus 100 may further include a biosignal detection command unit 180. When the subject intends to obtain biometric information, the biosignal detection command unit 180 may give a command for starting biosignal detection. Alternatively, the biosignal detection command unit 180 may configure a setting for detecting a biosignal from the subject periodically, for example, every hour or every two hours. The biosignal detection command unit 180 may be configured for the subject to select a detection cycle. Although FIG. 10 illustrates the processor 130 and the biosignal detection command unit 180 separately, the biosignal detection command unit 180 may be integrated with the processor 130.

Figure 11:
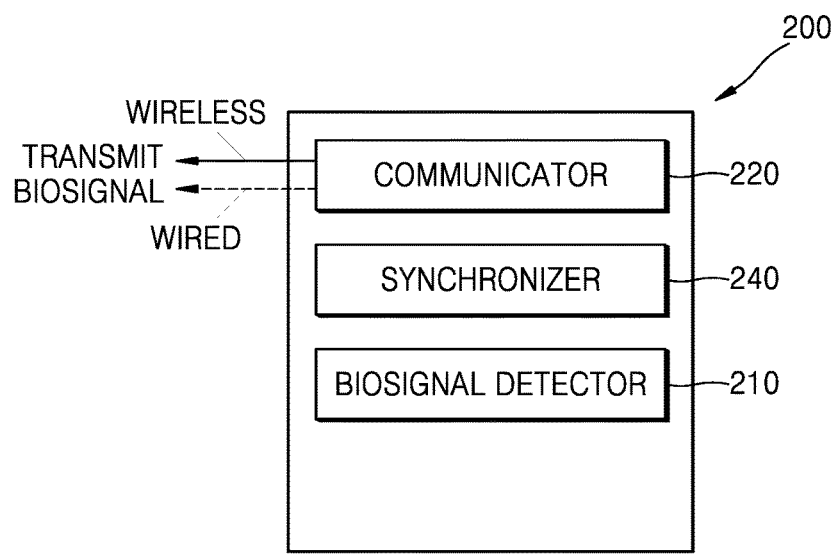
FIG. 11 schematically illustrates an apparatus for analyzing a biosignal, according to another exemplary embodiment.

FIG. 11 schematically illustrates an apparatus 200 for analyzing a biosignal, according to another exemplary embodiment. The apparatus 200 may include a biosignal detector 210, a communicator 220 transmitting a biosignal detected by the biosignal detector 210 to another device, and a synchronizer 240 for matching a point of time when the biosignal detector 210 detects the biosignal with a point of time when the other device detects a biosignal.

Descriptions of the biosignal detector 210 are substantially identical to those given with reference to FIGS. 1 to 5. Therefore, a detailed description thereof will be omitted below.

The communicator 220 may communicate with another device. For example, the communicator 220 may transmit a biosignal detected by the biosignal detector 210 to the other device. In this regard, the other device may be a separate apparatus independent from an apparatus including the biosignal detector 210. For example, the apparatus 200 may be applied to a portable terminal carried by the subject, and the other device may be a wearable terminal worn by the subject. Alternatively, the apparatus 200 may be applied to a wearable terminal worn by the subject, and the other device may be a portable terminal carried by the subject. The communicator 220 may receive a biosignal from the outside and may also transmit a biosignal to the other device. The communicator 220 may transmit and receive biosignals via wired or wireless communication.

The synchronizer 240 may synchronize a biosignal and another biosignal with respect to a time point when the biosignal detector 210 detects the biosignal and a time point when the other device detects the other biosignal so that a correlation expression may be extracted therefrom by combining the biosignals.

The synchronizer 240 may receive a synchronization signal from the other device, and the biosignal detector 210 may detect a biosignal based on the synchronization signal. The synchronizer 240 may also generate a synchronization signal and transmit the synchronization signal to the other device.

Figure 12:
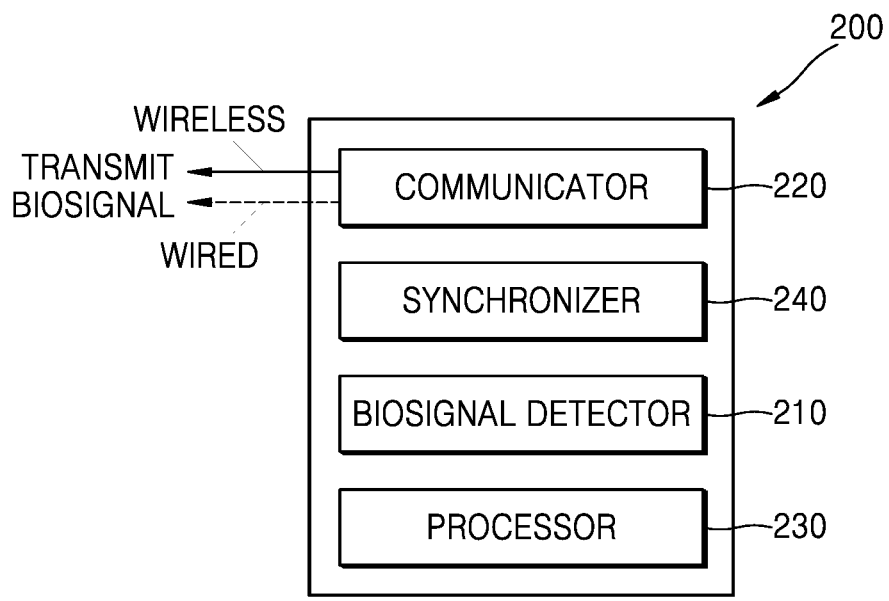
FIG. 12 illustrates an example in which a processor is further provided in the apparatus of FIG. 11.
Figure 13:
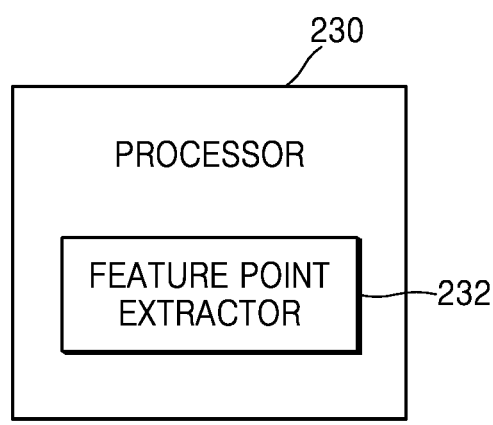
FIG. 13 illustrates an example of the processor of the apparatus of FIG. 12.

FIG. 12 illustrates an example in which a processor 230 is further provided in the apparatus 200 of FIG. 11. The processor 230 may process a signal detected by the biosignal detector 210. For example, as shown in FIG. 13, the processor 230 may include a feature point extractor 232 extracting feature points from a detected biosignal. For example, when a pulse wave signal is detected as a biosignal, the feature point extractor 232 of the processor 230 may extract feature points (refer to FIG. 5) from a detected pulse wave. The feature points may include, for example, at least one of a peak point and an inflection point in a pulse wave signal graph. The communicator 220 may transmit the biosignal or the feature points extracted by the feature point extractor 232 to the other device.

Figure 14:
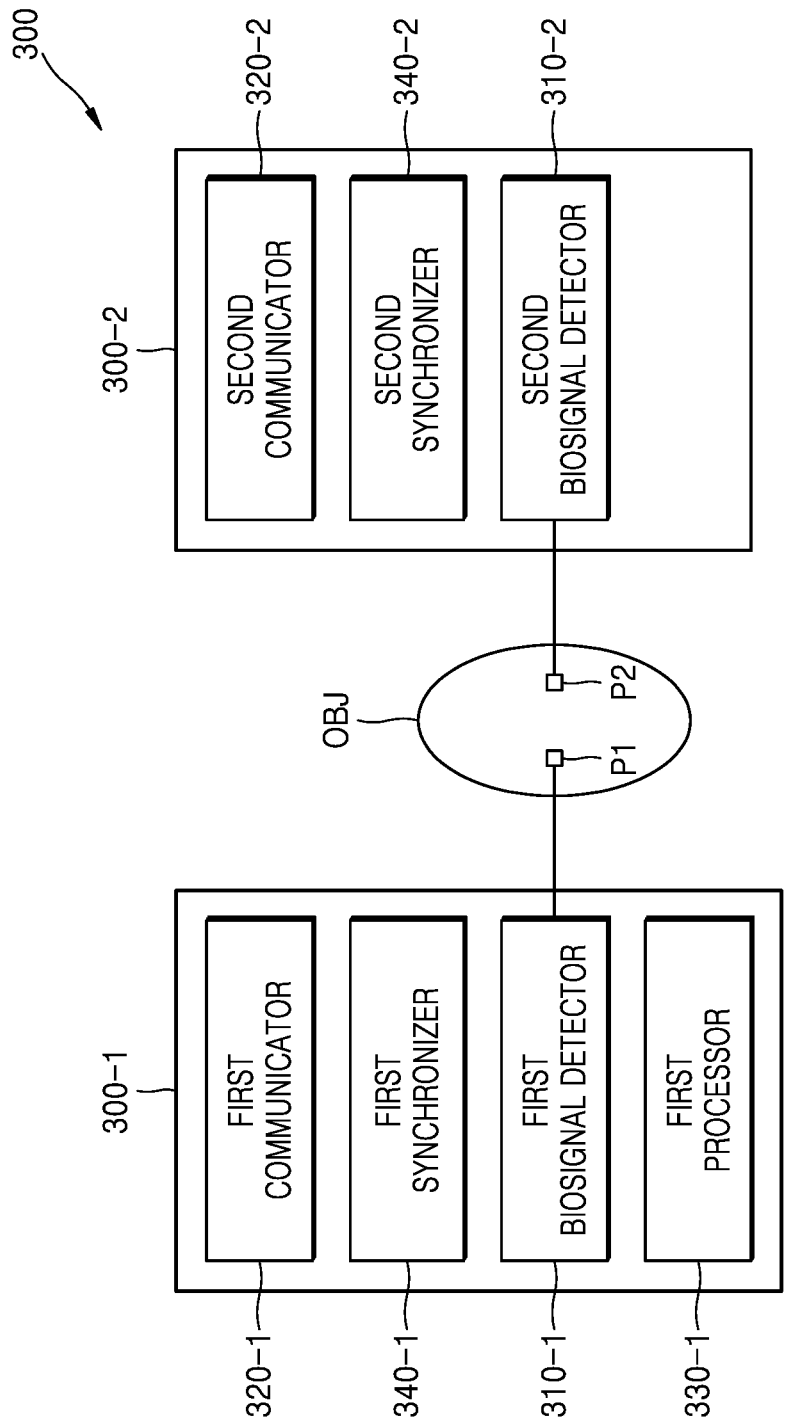
FIG. 14 schematically illustrates an apparatus for analyzing a biosignal, according to another exemplary embodiment.

FIG. 14 schematically illustrates an apparatus 300 for analyzing a biosignal, according to another exemplary embodiment.

The apparatus 300 may include a first apparatus 300-1 and a second apparatus 300-2 independent from each other. Independent apparatuses may refer to different types of apparatuses, apparatuses physically separate from one another, or apparatuses independently operated or controlled from one another. For example, the first apparatus 300-1 may be a portable mobile apparatus carried by a subject, and the second apparatus 300-2 may be a wearable apparatus worn by the subject.

The first apparatus 300-1 may include a first biosignal detector 310-1 detecting a first biosignal at a first point P1 of an object OBJ, a first communicator 320-1 communicating with the second apparatus 300-2, and a first processor 330-1 processing the first biosignal. When the first biosignal detector 310-1 detects the first biosignal, the first point P1 may be in contact with the subject or in the proximity of the subject.

The second apparatus 300-2 may include a second biosignal detector 310-2 detecting a second biosignal at a second point P2 of the object OBJ, and a second communicator 320-2 communicating with the first apparatus 300-1. When the second biosignal detector 310-2 detects the second biosignal, the second point P2 may be in contact with the subject or within a predetermined distance range from the subject.

The first apparatus 300-1 and the second apparatus 300-2 may respectively include a first synchronizer 340-1 and a second synchronizer 340-2 for synchronizing the first biosignal detector 310-1 and the second biosignal detector 310-2.

Each of the first and second synchronizers 340-1 and 340-2 may generate a synchronization signal or receive a synchronization signal. When the first processor 330-1 analyzes and processes a biosignal, the first synchronizer 340-1 may generate a synchronization signal, and the second synchronizer 340-2 may receive the synchronization signal. The first biosignal detector 310-1 and the second biosignal detector 310-2 may detect biosignals at the first point P1 and the second point P2 synchronized with each other by the first synchronizer 340-1 and the second synchronizer 340-2, respectively.

Although it is described in FIG. 14 that biometric information is obtained by using biosignals detected by two apparatuses, this is just an example, and the biometric information may be obtained by using biosignals detected by three or more independent apparatuses.

Each of the first and second biosignal detectors 310-1 and 310-2 may include the light-emitting unit 112 and the light-receiving unit 114, as described with reference to FIG. 2. However, a biosignal detector is not limited thereto, and may be configured to have one or more forms. A biosignal may include, for example, a pulse wave signal.

The second biosignal detected by the second biosignal detector 310-2 may be transmitted to the first communicator 320-1 by the second communicator 320-2, and the first communicator 320-1 may deliver the second biosignal to the first processor 330-1. The first biosignal detected by the first biosignal detector 310-1 may be sent to the first processor 330-1.

The first processor 330-1, for example, may compare the first biosignal and the second biosignal with each other and extract biometric information regarding an object from feature points of the first biosignal and the second biosignal. The first processor 330-1 may analyze feature points of pulse wave signals and obtain biometric information correlated to the feature points. For example, the first processor 330-1 may derive PTT and pulse wave velocity from the feature points. The pulse wave velocity may be derived from the PTT based on a distance between the first point P1 and the second point P2. The distance between the first point P1 and the second point P2 may be measured or estimated in one or more ways. For example, the subject may directly input a measurement of the distance between the first point P1 and the second point P2 to the first apparatus 300-1 or the second apparatus 300-2. Alternatively, data regarding states in which the first apparatus 300-1 and the second apparatus 300-2 are usually used may be collected to statistically determine the distance between the first point P1 and the second point P2. Alternatively, when the subject inputs conditions such as the subject's height and gender, a distance corresponding to the conditions may be determined. The distance between the first point P1 and the second point P2 may be derived by using one or more methods besides those described above. Biometric information which may be obtained from the biosignals may include at least one of blood pressure, blood vessel elasticity, blood viscosity, artery hardness, and blood flow rate.

Figure 15:
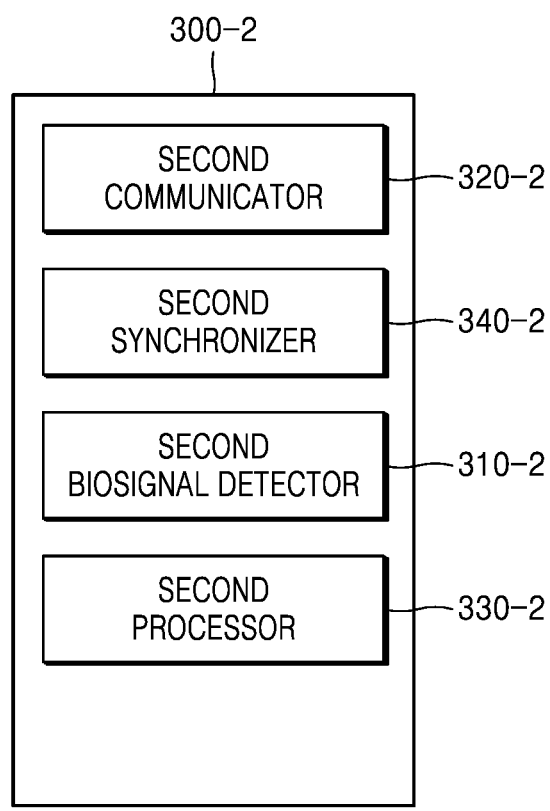
FIG. 15 illustrates another example of a second apparatus included in the apparatus of FIG. 14.
Figure 16:
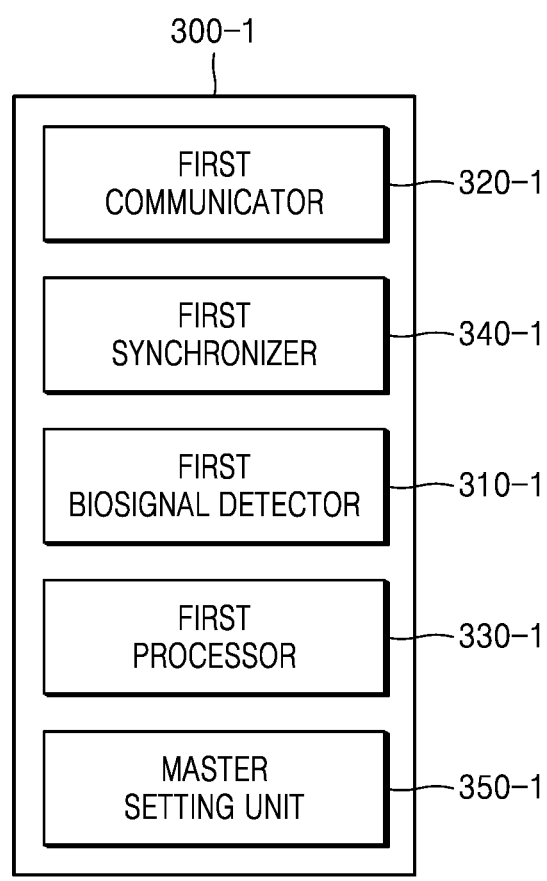
FIG. 16 illustrates another example of a first apparatus included in the apparatus of FIG. 14.

FIG. 15 illustrates an example in which the second apparatus 300-2 further includes a second processor 330-2. The second processor 330-2 may remove noise from the second biosignal detected by the second biosignal detector 310-2 or may perform first processing on the second biosignal to obtain biometric information. When a biosignal includes a pulse wave signal, the second processor 330-2, for example, may extract feature points (refer to FIG. 5) of the second biosignal. In addition, the second processor 330-2 may transmit data regarding the feature points of the second biosignal to the first apparatus 300-1. Alternatively, the second processor 330-2 may receive the first biosignal from the first apparatus 300-1 and may obtain biometric information from the first biosignal and the second biosignal. In this case, as illustrated in FIG. 16, a master setting unit 350-1 selecting the first apparatus 300-1 or the second apparatus 300-2 as a master apparatus for analyzing the biometric information may be further provided. Although it is illustrated in FIG. 16 that the master setting unit 350-1 is provided in the first apparatus 300-1, the master setting unit 350-1 may be provided in the second apparatus 300-2, or may be provided in both of the first apparatus 300-1 and the second apparatus 300-2. The master setting unit 350-1 may be configured for the subject to make a selection, for example, via an interface of the first apparatus 300-1. When the master setting unit 350-1 selects the first apparatus 300-1 as a master apparatus, the first apparatus 300-1 may receive the second biosignal from the second apparatus 300-2, analyze the first biosignal and the second biosignal, and derive biometric information therefrom. When the master setting unit 350-1 selects the second apparatus 300-2 as a master apparatus, the second apparatus 300-2 may receive the first biosignal from the first apparatus 300-1, analyze the first biosignal and the second biosignal, and derive biometric information therefrom. According to another exemplary embodiment, the master setting unit 350-1 may be incorporated into at least one of the first processor 330-1 and the second processor 330-2. Upon receipt of a user command, the first processor 330-1 and/or the second processor 330-2 may set either the first apparatus 300-1 or the second apparatus 330-2 as a master apparatus.

Figure 17:
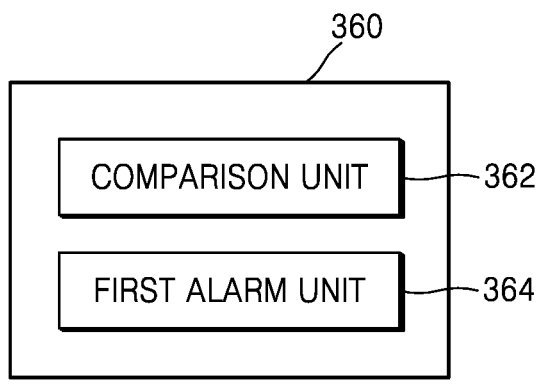
FIG. 17 schematically illustrates an error detection unit further included in the apparatus of FIG. 11.

Referring to FIG. 17, at least one of the first apparatus 300-1 and the second apparatus 300-2 may further include an error detection unit (e.g., error detector) 360. The error detection unit 360 may include a comparison unit (e.g., comparator) 362 comparing the first biosignal and the second biosignal with each other, and a first alarm unit 364 providing a notification of occurrence of an error when the comparison unit 362 determines that no valid feature points are detected from the first biosignal and the second biosignal. The first alarm unit 364 may inform the subject of the error via an alarm sound or by displaying an alarm screen. Although the error may occur for one or more reasons, the error may occur, for example, even when the first point P1 and the second point P2 are too far from each other.

Referring to FIG. 14, the first point P1 and the second point P2 may be two adjacent points of the object OBJ. For example, a distance between the first point P1 and the second point P2 is included in a range where valid biosignals may be detected. In this regard, the valid biosignals may be signals in a case in which signals that may be analyzed as substantially the same feature points are detected from the first biosignal and the second biosignal. For example, when the first apparatus 300-1 and the second apparatus 300-2 are respectively a smartphone and a smartwatch, and the subject holds the smartphone in his or her right hand and wears the smartwatch around his or her left wrist, a biosignal transit route of the subject is too long, and accordingly, valid biosignals may be difficult to detect. In this case, the error detection unit 360 may inform the subject of error occurrence so that the first apparatus 300-1 and the second apparatus 300-2 may be disposed adjacent to each other.

That is, when the subject wears the smartwatch around his or her left wrist, the subject may be led to hold the smartphone in his or her corresponding hand (e.g., left hand).

Figure 18:
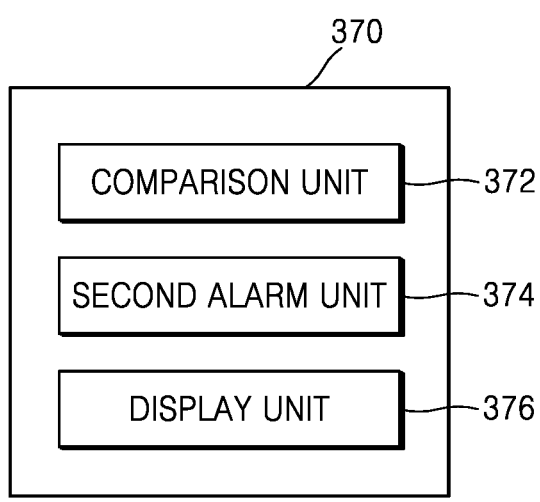
FIG. 18 schematically illustrates a healthcare unit further included in the apparatus of FIG. 11.

Referring to FIG. 18, at least one of the first apparatus 300-1 and the second apparatus 300-2 may further include a healthcare unit 370 managing the subject's health. The healthcare unit 370 may include a memory 372 storing biosignals and pieces of biometric information obtained from the first processor 330-1 or the second processor 330-2. For example, the memory 372 may store date and time when biosignals are detected, biometric information, and the like. At least one of the first apparatus 300-1 and the second apparatus 300-2 may calculate an average biometric information range of an object from the stored pieces of biometric information and store the average biometric information range of the object in the memory 372. For example, when ten or more pieces of biometric information regarding the object are stored, an average value thereof may be calculated, and a predetermined average biometric information range may be calculated with respect to the average value and stored. Alternatively, the memory 372 may store a normal range of biometric information. For example, when the biometric information includes blood pressure, the memory 372 may include a normal blood pressure range.

The healthcare unit 370 may further include a second alarm unit 374. The second alarm unit 374 may provide a notification to the subject when obtained biometric information is outside the average biometric information range. A notification that the obtained biometric information is beside the average biometric information range of the subject may indicate that the subject has encountered an unexpected situation. The second alarm unit 374 may also provide a notification to the subject when obtained biometric information is outside the normal biometric information range.

The second alarm unit 374 may warn the subject of an abnormal biometric information analysis result by using a sound alarm, a text alarm, or the like.

The healthcare unit 370 may further include a display unit 376 displaying obtained biometric information. The display unit 376 may display the obtained biometric information, and may also display alarm text generated by the second alarm unit 374 regarding abnormal biometric information Thus, the subject may be able to frequently check his or her health.

Figure 19:
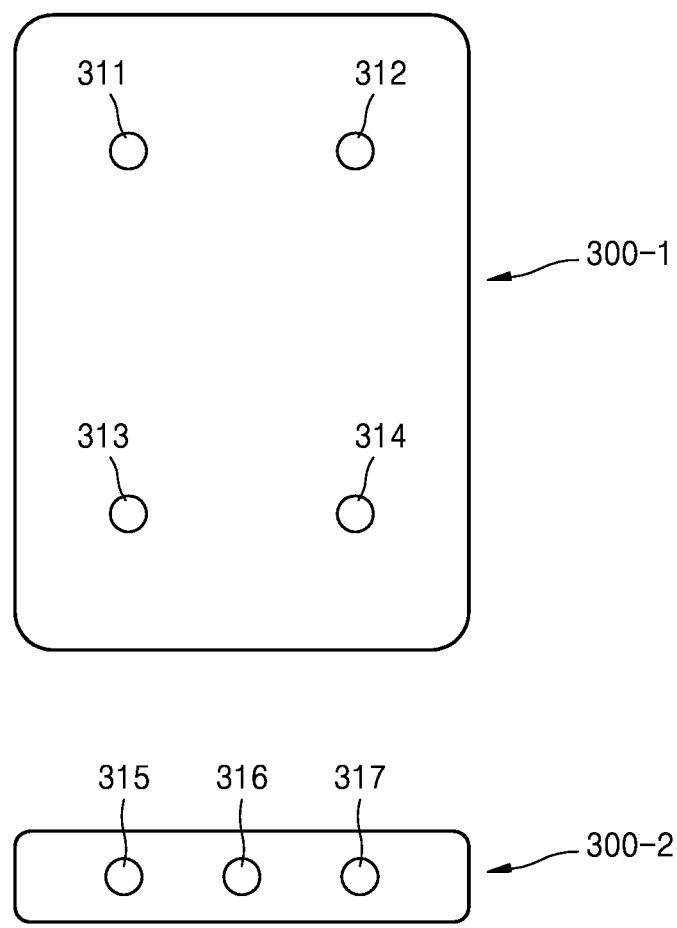
FIG. 19 illustrates an example in which a plurality of biosignal detectors are provided in each of a first apparatus and a second apparatus of the apparatus of FIG. 11.

Referring to FIG. 19, at least one of the first apparatus 300-1 and the second apparatus 300-2 may include a plurality of biosignal detectors. The first apparatus 300-1 and the second apparatus 300-2 may include the biosignal detectors, thereby decreasing cases in which no biosignals are detected as biosignal detectors are not brought into contact with the subject or the biosignal detectors are not within a proximity range (e.g., 1 cm) from the subject. For example, the first apparatus 300-1 may include 1-1, 1-2, 1-3, 1-4 biosignal detectors 311, 312, 313, and 314. The second apparatus 300-2 may include 2-1, 2-2, 2-3 biosignal detectors 315, 316, and 317.

Figure 20:
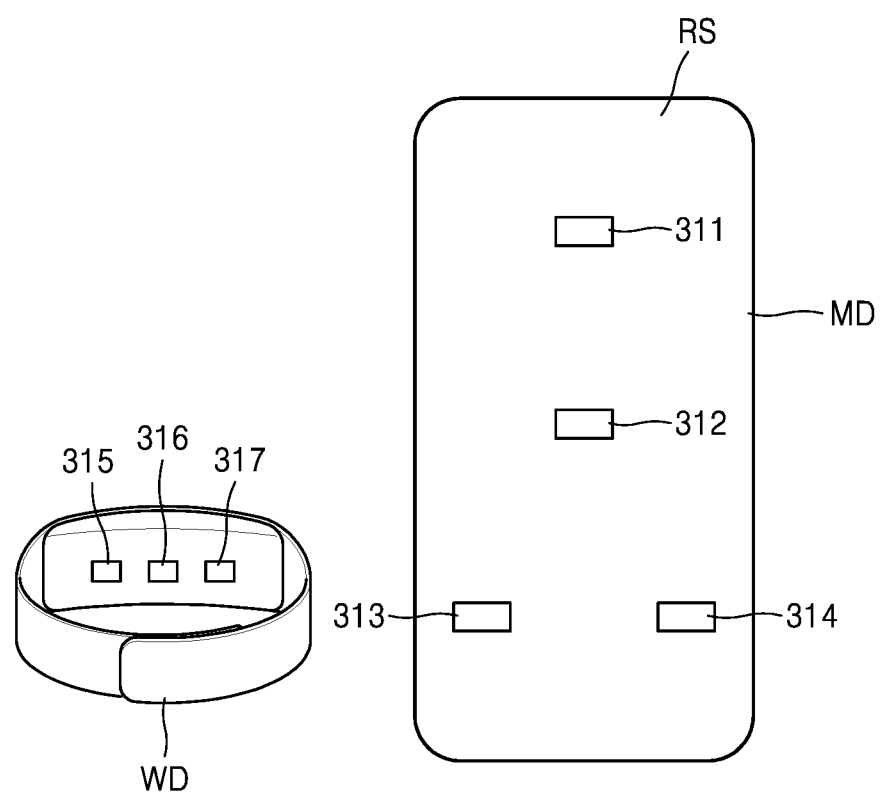
FIG. 20 illustrates an example in which a first apparatus and a second apparatus of an apparatus for analyzing a biosignal are respectively applied to a smartphone and a smartwatch, according to an exemplary embodiment.

The 1-1, 1-2, 1-3, 1-4 biosignal detectors 311, 312, 313, and 314 may be disposed on the first apparatus 300-1 and spaced apart from each other. For example, when the first apparatus 300-1 is applied to a portable mobile device MD, for example, a smartphone, as illustrated in FIG. 20, the 1-1, 1-2, 1-3, 1-4 biosignal detectors 311, 312, 313, and 314 may be disposed on a rear surface RS of the mobile device MD. However, positions of the 1-1, 1-2, 1-3, 1-4 biosignal detectors 311, 312, 313, and 314 are not limited thereto, and the 1-1, 1-2, 1-3, 1-4 biosignal detectors 311, 312, 313, and 314 may be disposed at one or more positions of an area of the mobile device MD that may be brought into contact with the subject when the subject uses the mobile device MD. For example, the 1-1, 1-2, 1-3, 1-4 biosignal detectors 311, 312, 313, and 314 may be disposed on a lateral surface of the mobile device MD.

For example, as illustrated in FIG. 20, the 1-1 biosignal detector 311 may be disposed on an upper central portion of the rear surface RS of the mobile device MD, the 1-2 biosignal detector 312 may be disposed on a central portion of the rear surface RS, the 1-3 biosignal detector 313 may be disposed on a lower left side of the rear surface RS, and the 1-4 biosignal detector 314 may be disposed on a lower right side of the rear surface RS. However, such a disposition structure is just an example, and may be modified in one or more ways. Also, when the second apparatus 300-2 is applied to a wearable mobile device WD, the 2-1, 2-2, 2-3 biosignal detectors 315, 316, and 317 may be disposed on an inner lateral surface of the wearable mobile device WD to be spaced apart from each other. For example, when the wearable mobile device WD is a smartwatch, the 2-1, 2-2, 2-3 biosignal detectors 315, 316, and 317 may be disposed on an inner lateral surface of the smartwatch that is brought into contact with skin of the subject when the subject wears the smartwatch.

Figure 21:
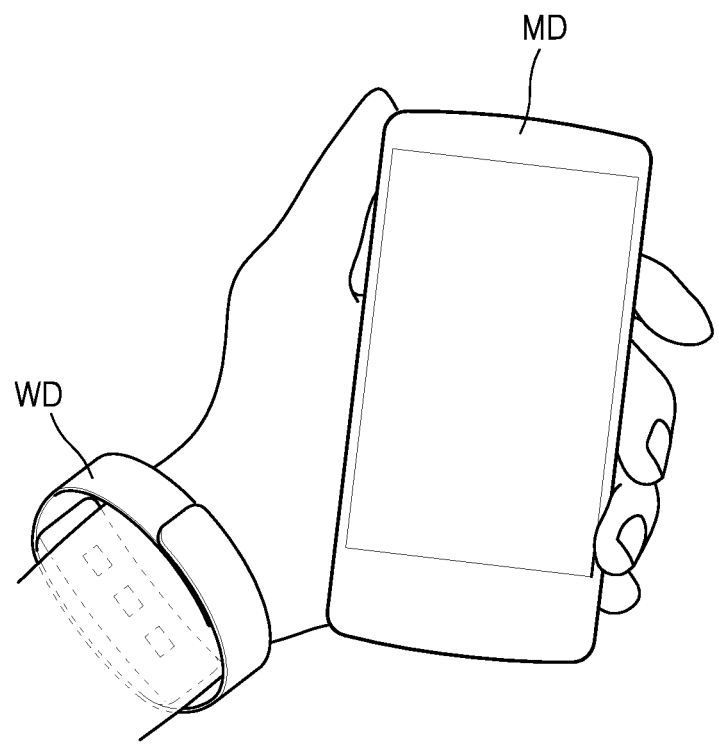
FIG. 21 illustrates a subject using a smartphone and wearing a smartwatch.

FIG. 21 illustrates an example in which the subject uses a smartphone and a smartwatch together. When the subject uses the smartphone holding the smartphone in his or her hand, at least one of the 1-1, 1-2, 1-3, 1-4 biosignal detectors 311, 312, 313, and 314 disposed on a rear side of the smartphone may come into contact with the subject's hand. In addition, when the subject wears the smartwatch, at least one of the 2-1, 2-2, 2-3 biosignal detectors 315, 316, and 317 disposed on an inner lateral surface of the smartwatch may come into contact with the subject's skin.

In this regard, as described above, an error detection unit (refer to the error detection unit 360 of FIG. 17) may provide a notification to the user instructing the user to carry the smartphone and wear the smartwatch on a same hand so that valid biosignals may be obtained (e.g., a notification instructing the user to carry the smartphone in his or her left hand while wearing the smartwatch on his or her left wrist).

Figure 22:
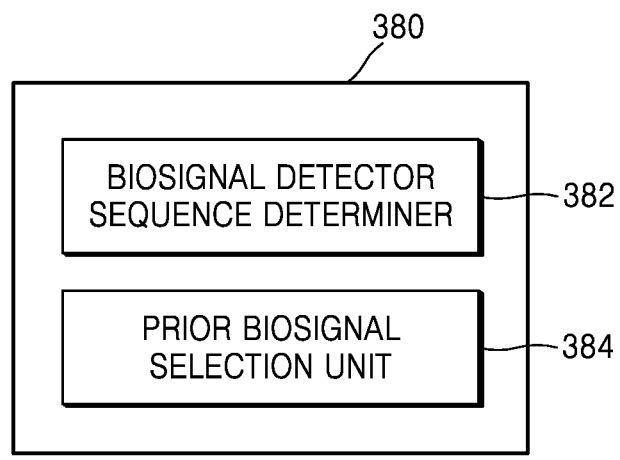
FIG. 22 illustrates an example of a biosignal detector selection unit further included in at least one of a first apparatus and a second apparatus of an apparatus for analyzing a biosignal, according to an exemplary embodiment.

As illustrated in FIG. 22, at least one of the first apparatus 300-1 and the second apparatus 300-2 may further include a biosignal selection unit 380 selecting valid biosignals for analysis from among biosignals detected by biosignal detectors. In this regard, the valid biosignals may refer to biosignals used to obtain biometric information. The biosignal selection unit 380 may include, for example, a biosignal detector sequence determiner 382 determining a sequence of a plurality of biosignal detectors. The biosignal detector sequence determiner 382 may set a sequence in which valid biosignal detectors are selected from among the biosignal detectors. Such a sequence may be determined, for example, according to the position of a biosignal detector or according to the accuracy of a biosignal. A sequence according to the positions of the biosignal detectors may be determined, for example, based on the frequency in which the subject contacts each of the biosignal detectors. Alternatively, a sequence according to the accuracy of the biosignals may be determined by measuring the accuracy of biosignals with respect to the location of the subject which each of the biosignal detectors contacts, and the sequence of the valid biosignal detectors may be determined according to such a sequence.

The biosignal selection unit 380 may further include a prior biosignal selection unit 384 selecting a biosignal having priority from among biosignals detected according to a sequence set by the biosignal detector sequence determiner 382. For example, the first apparatus 300-1 may include the 1-1, 1-2, 1-3, 1-4 biosignal detectors 311, 312, 313, and 314, and the 1-1, 1-2, 1-3, 1-4 biosignal detectors 311, 312, 313, and 314 may be sequentially set as first-rank, second-rank, third-rank, and fourth-rank. In addition, in a case in which biosignals are detected only by the 1-2, 1-3 biosignal detectors 312 and 313 when the subject uses the first apparatus 300-1, the biosignal detected by the 1-2 biosignal detector 312 from among the detected biosignals may have priority.

The second apparatus 300-2 may include the 2-1, 2-2, 2-3 biosignal detectors 315, 316, and 317, and the 2-1, 2-2, 2-3 biosignal detectors 315, 316, and 317 may be sequentially set as first-rank, second-rank, and third-rank. In addition, in a case in which biosignals are detected only by the 2-2, 2-3 biosignal detectors 316 and 317 when the subject uses the second apparatus 300-2, the biosignal detected by the 2-2 biosignal detector 316 from among the detected biosignals may have priority. In this case, the biosignal detected by the 1-2 biosignal detector 312 and the biosignal detected by the 2-2 biosignal detector 316 may be used to obtain biometric information. For example, the biosignals may include pulse wave signals, and the biometric information may include pulse wave velocity.

Alternatively, the prior biosignal selection unit 384 may select some or all of a plurality of detected biosignals. For example, biosignals may be analyzed by using all possible combinations regarding a plurality of biosignals detected by the first apparatus 300-1 and a plurality of biosignals detected by the second apparatus 300-2. In addition, an average value of pieces of biometric information based on a biosignal analysis result according to those combinations may be derived as valid biometric information. Likewise, a biosignal analysis result obtained by using plural combinations may be used, and thus, accuracy of biometric information may be increased.

Figure 23:
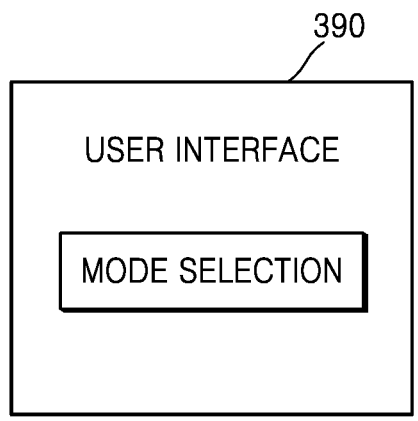
FIG. 23 illustrates an example of a mode selection unit further included in at least one of a first apparatus and a second apparatus of an apparatus for analyzing a biosignal, according to an exemplary embodiment.

As illustrated in FIG. 23, at least one of the first apparatus 300-1 and the second apparatus 300-2 may further include a mode selection unit 390. The mode selection unit 390, for example, may select one of a mode of obtaining biometric information from two independent apparatuses (first mode) and a mode of obtaining biometric information from the same apparatus (second mode). For example, when at least one of the first apparatus 300-1 and the second apparatus 300-2 includes a plurality of biosignal detectors, as described above, biometric information may be obtained by using biosignals detected by the first apparatus 300-1 and biosignals detected by the second apparatus 300-2. Alternatively, biometric information may be obtained by using only a plurality of biosignals detected by biosignal detectors of the first apparatus 300-1. Alternatively, biometric information may be obtained by using only a plurality of biosignals detected by biosignal detectors of the second apparatus 300-2. Accordingly, obtaining biometric information by using the biosignals detected by each of the first apparatus 300-1 and the second apparatus 300-2 (first mode) and obtaining biometric information by using the biosignals detected by the first apparatus 300-1 or the second apparatus 300-2 (second mode) are available, and therefore, the subject may select and use one of the first mode and the second mode.

The mode selection unit 390 may be implemented via user interfaces of the first apparatus 300-1 and the second apparatus 300-2. For example, the mode selection unit 390 may be implemented via mode selection icons of the user interfaces so that a user may easily select a mode. In this regard, although the user may be an object from which biometric information is to be measured, that is, the subject, the user may refer to one who may use an apparatus for analyzing a biosignal, such as a medical professional, but is not limited thereto. Via the user interfaces, information necessary for operating an apparatus for analyzing a biosignal may be input, and an analysis result may be output. The user interfaces may include, for example, buttons, connectors, keypads, display units, etc. In some exemplary embodiments, the user interfaces may further include configurations such as sound output units or vibration motors.

Likewise, when biometric information is obtained by using biosignals detected by two apparatuses independent and separate from each other, width of selection may be increased compared to when one apparatus is used, and degree of freedom in a method of detecting a biosignal may be increased. Further, since each of the two apparatuses includes a biosignal detector, a processor, or the like, a system for analyzing a biosignal may be partitioned into smaller sizes of apparatuses, and the degree of freedom in manufacturing the apparatus may be increased. Accordingly, productivity may be increased.

Figure 24:
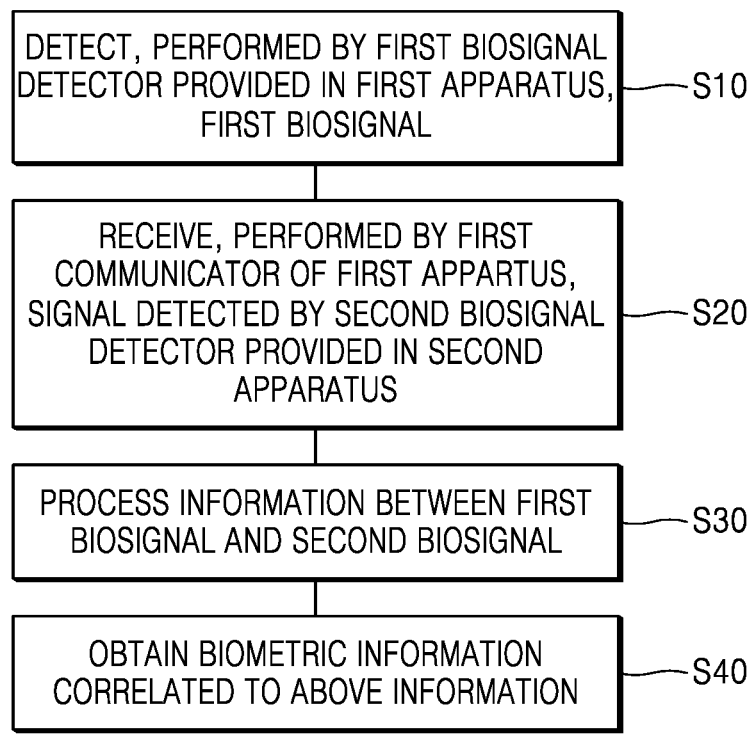
FIG. 24 is a diagram for describing a method of analyzing a biosignal, according to an exemplary embodiment.

FIG. 24 is a diagram for describing a method of detecting a biosignal, according to an exemplary embodiment. The method of detecting a biosignal will be described with reference to FIGS. 14 and 15.

According to the method of detecting a biosignal, biometric information may be analyzed by using biosignals detected by the first apparatus 300-1 and the second apparatus 300-2 which are independent and separate from each other.

In operation S10, a first biosignal may be detected by the first biosignal detector 310-1 provided in the first apparatus 300-1. In operation S20, the first communicator 320-1 of the first apparatus 300-1 may receive a second biosignal detected by the second biosignal detector 310-2 provided in the second apparatus 300-2.

In operation S30, the first processor 330-1 of the first apparatus 300-1 may analyze and process information between the first biosignal and the second biosignal. In operation S40, biometric information correlated to the information may be obtained. Likewise, a biosignal may be received from one apparatus, and another biosignal detected by another apparatus may be analyzed along with the received biosignal in the other apparatus, thereby obtaining useful biometric information.

Figure 25:
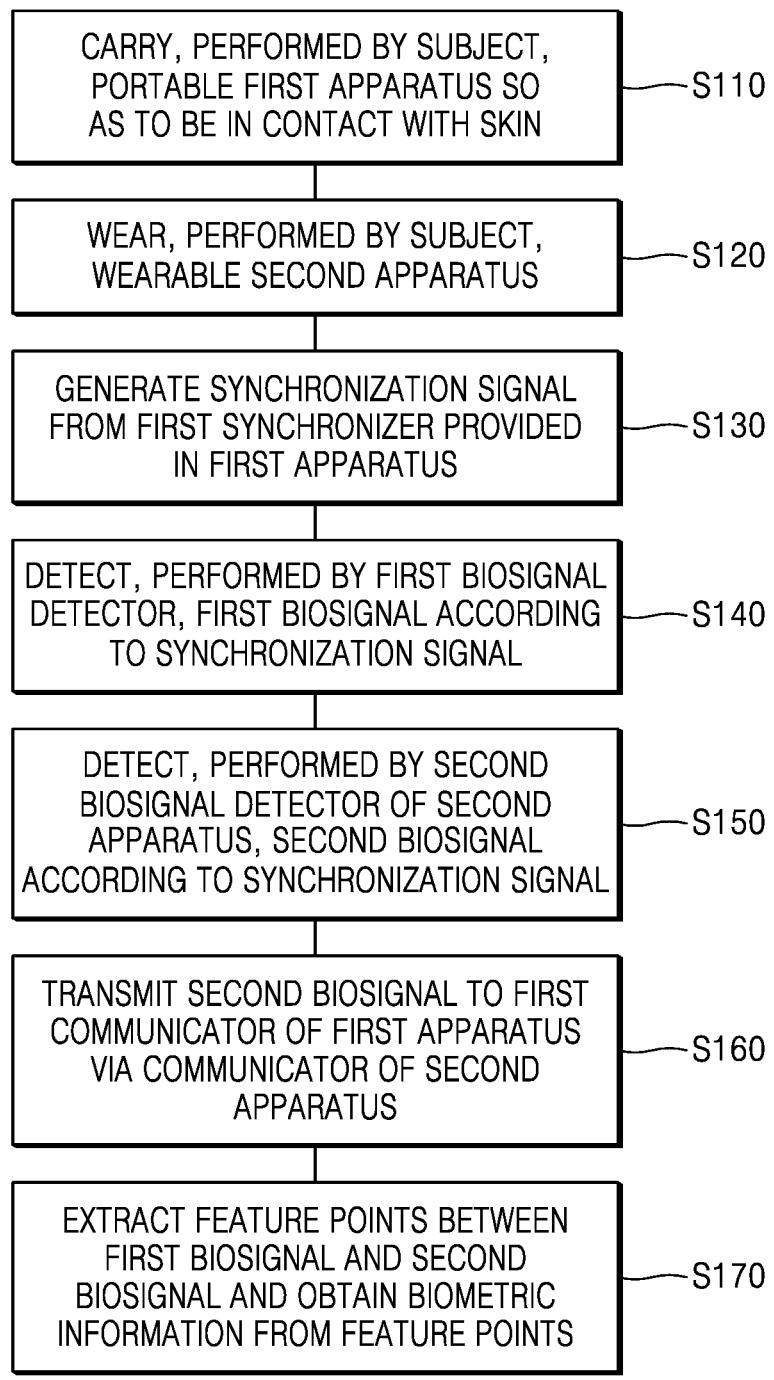
FIG. 25 is a diagram for describing a method of analyzing a biosignal, according to another exemplary embodiment.

FIG. 25 is a diagram for describing a method of detecting a biosignal, according to another exemplary embodiment. The method of detecting a biosignal will be described with reference to FIGS. 14 and 15.

In operation S110, a subject may carry the first apparatus 300-1 that is portable such that the first apparatus 300-1 is in contact with the skin of the subject, and in operation S120, the subject may wear the second apparatus 300-2 that is wearable such that the second apparatus 300-2 is adjacent to the first apparatus 300-1. In operation S130, a synchronization signal may be generated by the first synchronizer 340-1 provided in the first apparatus 300-1 and may be transmitted to the second apparatus 300-2. In operation S140, according to the synchronization signal, a first biosignal may be detected by the first biosignal detector 310-1 provided in the first apparatus 300-1. Also, in operation S150, according to the synchronization signal, a second biosignal may be detected by the second biosignal detector 310-2 provided in the second apparatus 300-2.

In addition, the first biosignal may be transmitted to the first processor 330-1 provided in the first apparatus 300-1. In operation S160, the second biosignal may be transmitted to the first communicator 320-1 of the first apparatus 300-1 by the second communicator 320-2 provided in the second apparatus 300-2. In operation S170, the first processor 330-1 may extract feature points between the first biosignal and the second biosignal, and biometric information may be obtained from the feature points.

According to the present exemplary embodiment, a range of choices may be increased compared to when one apparatus is used, and degrees of freedom in a method of detecting a biosignal may be increased.

As described above, people's health may be easily and frequently checked and managed with an non-invasive method by using an apparatus and method of detecting a biosignal, according to one or more exemplary embodiments.

The apparatus described herein may include a processor, a memory for storing and executing program data, a permanent storage such as a disk drive, a communication port for handling communication with an external apparatus, and user interface apparatuses such as a touch panel, a key, and a button. Methods implemented as software modules or algorithms may be stored as program instructions or computer-readable codes executable by a processor on a computer-readable medium. Examples of the computer-readable medium include a magnetic storage medium (e.g., read-only memory (ROM), random-access memory (RAM), floppy disk, or hard disk) and an optically readable medium (e.g., compact disk-read only memory (CD-ROM), or digital versatile disk (DVD)). The computer readable recording medium can also be distributed over network-coupled computer systems so that a computer-readable code is stored and executed in a distributed fashion. This medium may be read by the computer, stored in the memory, and executed by the processor.

One or more exemplary embodiments may be described in terms of functional block configurations and various processing steps. Such functional blocks may be realized by any number of hardware and/or software configurations performing specified functions. For example, the one or more exemplary embodiments may employ various integrated circuit configurations, such as memory elements, processing elements, logic elements, and look-up tables, which may carry out a variety of functions under the control of one or more microprocessors or other control apparatuses. As the components of the one or more exemplary embodiments are implemented using software programming or software elements, the one or more exemplary embodiments may be implemented using any programming or scripting language, such as C, C++, Java, or assembler, with various algorithms being implemented with any combination of data structures, processes, routines or other programming configurations. Functional aspects may be implemented using an algorithm executed by one or more processors. Furthermore, the one or more exemplary embodiments may employ the related art for electronic environment setting, signal processing and/or data processing, etc. The terms such as "mechanism", "element", "means", and "configuration" may be used broadly and are not limited to mechanical or physical configurations, but may include software routines in conjunction with processors, etc.

The particular implementations shown and described herein are illustrative examples and are not intended to otherwise limit the scope of the inventive concept in any way. For the sake of brevity, description of conventional electronic configurations, control systems, software, and other functional aspects of the systems may be omitted.

Furthermore, connecting lines or connectors between elements shown in the accompanying drawings are intended to represent exemplary functional connections and/or physical or logical connections between the elements. In a practical apparatus, a variety of alternative or additional functional connections, physical connections or logical connections may be present.

The terms "a", "an", and "the," and similar referents used herein (especially in the following claims) are to be construed to cover both the singular and the plural. Furthermore, recitation of ranges of values herein are merely intended to serve as a shorthand method of referring individually to each separate value falling within the range, unless otherwise indicated herein, and each separate value is incorporated into the specification as if it were individually recited herein.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An apparatus for analyzing a biosignal, the apparatus comprising:
   a communicator configured to receive from an external device a first biosignal of an object detected by the external device;
   a synchronizer configured to transmit a synchronization signal to the external device or receive the synchronization signal from the external device;
   at least one biosignal detector that comprises a light emitter configured to radiate light to the object, and a light receiver configured to receive the radiated light returned from the object to detect a second biosignal of the object from the received light according to the synchronization signal; and
   a processor configured to compare characteristics of the first biosignal and the second biosignal and obtain biometric information having correlation with a result of the comparison,
   wherein the at least one biosignal detector radiates and receives the light to detect the second biosignal in response to a distance between a first measurement point of the object from which the first biosignal is detected by the external device and a second measurement point of the object from which the second biosignal is detected by the at least one biosignal detector of the apparatus being determined to be less than a predetermined distance.

2. The apparatus of claim 1, wherein the distance between the first measurement point and the second measurement point being determined to be less than the predetermined distance in response to the first measurement point and the second measurement point being respectively located at a left hand and a left wrist of the object, and
   the distance between the first measurement point and the second measurement point being determined to be less than the predetermined distance in response to the first measurement point and the second measurement point being respectively located at a right hand and a right wrist of the object.

3. The apparatus of claim 1, wherein the apparatus is portable or wearable by the object and the apparatus is independent from the external device.

4. The apparatus of claim 1, wherein the apparatus is a smartphone or a smartwatch.

5. The apparatus of claim 1, wherein the first biosignal and the second biosignal comprise pulse wave signals.

6. The apparatus of claim 5, wherein the processor is further configured to obtain a pulse wave velocity based on the characteristics of the first biosignal and the second biosignal.

7. The apparatus of claim 1, wherein the biometric information comprises at least one of blood pressure, blood vessel elasticity, blood viscosity, artery stiffness, and blood flow rate.

8. The apparatus of claim 1,
wherein the at least one biosignal detector comprises a plurality of biosignal detectors, and
wherein the apparatus further comprises a biosignal selection unit configured to select one of the plurality of biosignal detectors and control the selected biosignal detector to detect the second biosignal of the object while the selected biosignal detector is in contact with the object.

9. The apparatus of claim 1, further comprising a memory configured to store the obtained biometric information,
wherein the processor is further configured to determine an average biometric information range based on the stored biometric information and store the average biometric information range in the memory.

10. The apparatus of claim 9, further comprising an alarm unit configured to generate an alarm when newly obtained biometric information is outside the average biometric information range.

11. The apparatus of claim 1, wherein the processor is configured to obtain a pulse wave transit time between two points corresponding to a peak point of the first biosignal and a peak point of the second biosignal.

12. An apparatus for analyzing a biosignal, the apparatus comprising:
a first apparatus comprising at least one first biosignal detector configured to detect a first biosignal of an object and a first synchronization signal generator; and
a second apparatus comprising a first synchronization signal receiver configured to receive a synchronization signal from the first synchronization signal generator, at least one second biosignal detector configured to detect a second biosignal of the object according to the synchronization signal, and a first communicator configured to transmit the second biosignal to a first processor,
wherein the first apparatus further comprises the first processor configured to compare characteristics of the first biosignal and the second biosignal and obtain biometric information based on a result of the comparison, and
wherein the first biosignal detector detects the first biosignal in response to a distance between a first measurement point of the object from which the first biosignal is detected by the first apparatus and a second measurement point of the object from which the second biosignal is detected by the second apparatus being determined to be less than a predetermined distance.

13. The apparatus of claim 12, wherein the first apparatus further comprises a second receiver and a second communicator, the second apparatus further comprises a second synchronization signal generator and a second processor, and at least one of the first apparatus and the second apparatus further comprises a master setting unit configured to select a master processor performing signal processing from among the first processor and the second processor.

14. The apparatus of claim 12, wherein the first apparatus and the second apparatus are different mobile apparatuses.

15. The apparatus of claim 12, wherein at least one of the first apparatus and the second apparatus is a wearable mobile apparatus.

16. The apparatus of claim 12, wherein one of the first apparatus and the second apparatus is wearable by the object, and
the other one of the first apparatus and the second apparatus is a portable apparatus which is in contact with the object while the first biosignal or the second biosignal is detected.

17. The apparatus of claim 16, wherein the first apparatus is a mobile apparatus portable by the object, and the second apparatus is a mobile apparatus wearable by the object.

18. The apparatus of claim 12, wherein the first apparatus further comprises a first biosignal selection unit,
wherein the at least one first biosignal detector comprises a plurality of first biosignal detectors that contact the object, and
the first biosignal selection unit selects one of the plurality of first biosignal detectors and controls the selected first biosignal detector to detect the first biosignal.

19. The apparatus of claim 12, wherein the at least one second biosignal detector comprises a plurality of second biosignal detectors, and
wherein the second apparatus further comprises a second biosignal selection unit configured to select one of the plurality of second biosignal detectors and control the selected second biosignal detector to detect the second biosignal.

20. A method of analyzing a biosignal by a first apparatus, the method comprising:
detecting a first biosignal by a first biosignal detector of the first apparatus;
receiving, at a second apparatus, a second biosignal detected by the second apparatus;
comparing characteristics of the detected first bio signal and the received second biosignal by a processor of the first apparatus; and
obtaining biometric information from a result of the comparison by the processor,
wherein the first biosignal is detected by the first biosignal detector in response to a distance between a first measurement point of an object from which the first biosignal is detected by the first apparatus and a second measurement point of the object from which the second biosignal is detected by the second apparatus being determined to be less than a predetermined distance.

21. A method of analyzing a biosignal of an object by a first apparatus and a second apparatus which is provided separately from the first apparatus, the method comprising:
generating a synchronization signal by a first synchronizer of the first apparatus;
detecting a first biosignal according to the synchronization signal by a first biosignal detector of the first apparatus while the first apparatus is in contact with the object;
detecting a second biosignal according to the synchronization signal by a second biosignal detector of the second apparatus in response to a distance between a first measurement point of the object from which the first biosignal is detected by the first apparatus and a second measurement point of the object from which the second biosignal is detected by the second apparatus being determined to be less than a predetermined distance;

transmitting the second biosignal from the second apparatus to the first apparatus;
extracting, by a first processor of the first apparatus, a first feature point of the first biosignal and a second feature point of the second biosignal that corresponds to the second feature point; and
obtaining biometric information based on the first feature point and the second feature point.

* * * * *